US008011227B2

(12) United States Patent
Olsen et al.

(10) Patent No.: US 8,011,227 B2
(45) Date of Patent: Sep. 6, 2011

(54) DETECTION OF INGRESS OF WATER IN AN INTERMEDIATE LAYER USING ACOUSTIC RESONANCE TECHNOLOGY

(75) Inventors: Åge A. Olsen, Ingeberg (NO); Jostein Jacobsen, Lommedalen (NO); Tore Magne Halås Skar, Borgen (NO); Petter Norli, Oslo (NO); Ashild Bergh, Drammen (NO); Nils-Otto Negård, Vøyenenga (NO); Steinar Låg, Hvalstad (NO)

(73) Assignee: Det Norske Veritas AS, Hovik (NO)

( * ) Notice: Subject to any disclaimer, the term of this patent is extended or adjusted under 35 U.S.C. 154(b) by 446 days.

(21) Appl. No.: 12/209,227

(22) Filed: Sep. 12, 2008

(65) Prior Publication Data

US 2009/0064770 A1     Mar. 12, 2009

Related U.S. Application Data

(60) Provisional application No. 60/971,684, filed on Sep. 12, 2007.

(30) Foreign Application Priority Data

Sep. 12, 2007   (NO) .................................. 20074644

(51) Int. Cl.
*G01M 3/04*       (2006.01)
(52) U.S. Cl. ................................... 73/40.5 A
(58) Field of Classification Search ............... 73/40.5 A, 73/592
See application file for complete search history.

(56) References Cited

U.S. PATENT DOCUMENTS

| | | | | |
|---|---|---|---|---|
| 3,981,181 A * | 9/1976 | Ochiai | ....................... | 73/40.5 R |
| 4,289,019 A * | 9/1981 | Claytor | ....................... | 73/40.5 A |
| 4,574,615 A * | 3/1986 | Bower et al. | .................. | 73/24.01 |
| 4,797,621 A * | 1/1989 | Anderson et al. | ............. | 324/533 |
| 5,078,006 A * | 1/1992 | Maresca et al. | ............ | 73/40.5 R |
| 5,117,676 A | 6/1992 | Chang | | |
| 5,134,377 A * | 7/1992 | Reddy et al. | .................. | 324/533 |
| 7,134,319 B2 | 11/2006 | Liu | | |

FOREIGN PATENT DOCUMENTS

| | | |
|---|---|---|
| JP | 11-132896 A | 5/1999 |
| WO | 2005/008236 A1 | 1/2005 |

* cited by examiner

*Primary Examiner* — Hezron Williams
*Assistant Examiner* — Nathaniel Kolb
(74) *Attorney, Agent, or Firm* — Young & Thompson

(57) ABSTRACT

An apparatus and a method for determining a moisture ingress in an insulating layer surrounding a pipe, the insulating layer being surrounded by a tubular jacket. The apparatus includes an acoustic transducer in communication with an exciter adapted to provide a brief and broad banded acoustic signal which includes frequencies which by their propagation in the material of the jacket has a wavelength which corresponds to twice the thickness of the jacket or an odd multiple of twice the thickness of the jacket, and to process a reverberation signal emitted from the jacket in response to sending into the jacket the brief and broad banded output signal from the transducer. The signal processor is adapted to make a frequency analysis of the received reverberation signal for producing a frequency response curve, to establish features of the frequency response curve which are characteristic of a moisture content in the insulation material on the inside of the jacket, and to output an indication being specific for the moisture ingress.

8 Claims, 8 Drawing Sheets

DETECTION OF INGRESS OF WATER IN AN INTERMEDIATE LAYER USING ACOUSTIC RESONANCE TECHNOLOGY

1 INTRODUCTION

Figure 5:
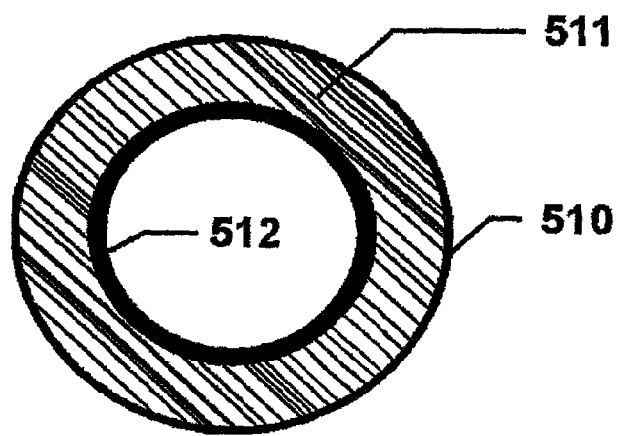

The purpose of the present invention is to detect water ingress in the intermediate layer of a measurement object, having a cylindrical sandwich structure, such as that shown in FIG. 5. Such piping structures are in use at the Kårstø gas refinery in Norway, and quested to be characterized by the present technique. Another relevant measurement object to characterize is sketched in FIG. 6.

Generally, these measurement objects comprise an outermost solid material layer 510 FIG. 5, which is significantly thinner than the internal layer; an intermediate layer 511, having different acoustical impedance than the adjacent layers; and an internal solid material layer 512. It is required that the thickness of the outermost layer is such that the SNR of the received half-wave resonance tail (FIG. 4) can be made sufficient from which to extract thickness characteristics.

The method may alternatively be applied to characterize only parts of the described sandwich structure, such as the outermost layer 510 and possibly the intermediate layer 511. The method might also be applied for cases in which either the outermost layer 510 or internal layers 512 are covered with coatings, or are corroded. In the latter case, several measurements will be utilized to smear out the presumed random nature of the corrosion topology, cf. Sec. 3.4, block 1040.

2 THE DRAWINGS

Figure 1:
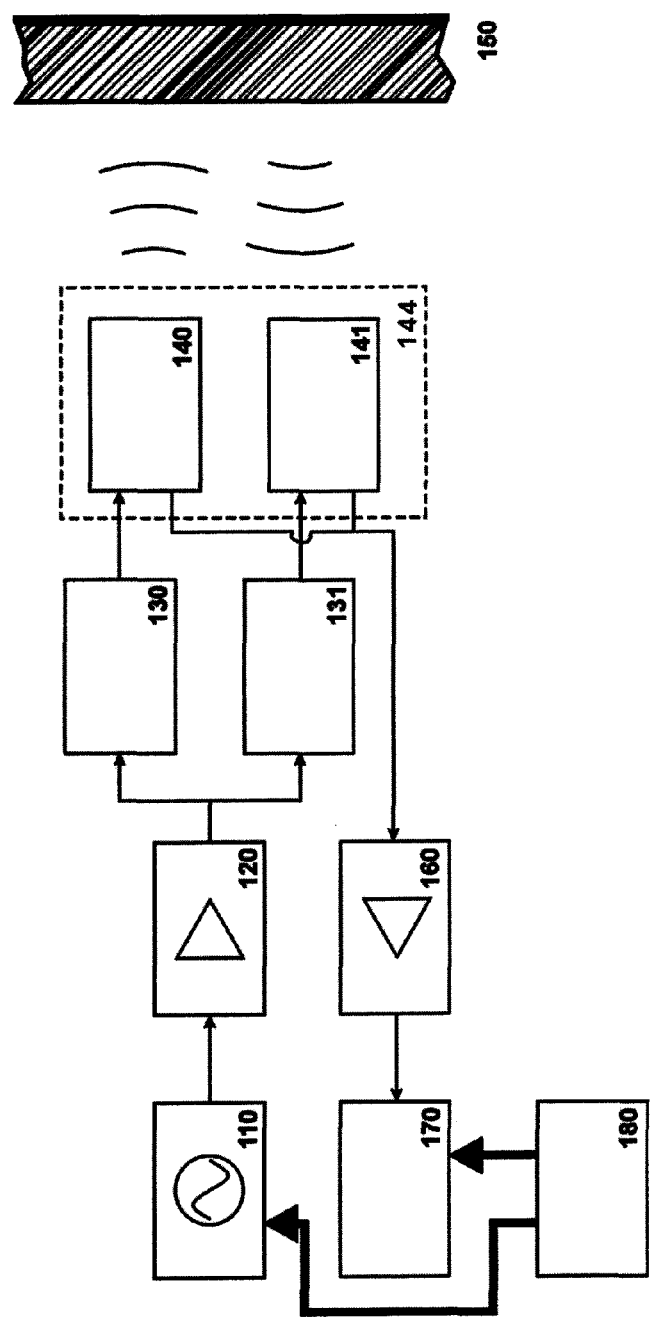

FIG. 1. Functional diagram of measurement setup for detection of water ingress in intermediate layer. The labels refer to the following: 110 function generator; 120 power amplifier; 130 LF transmitting matching filer; 131 HF transmitting matching filter; 140 LF ultrasonic transceiver; 141 HF ultrasonic transceiver; 150 measurement object; 160 preamplifier; 170 data acquisition system; 180 control PC.

Figure 2:
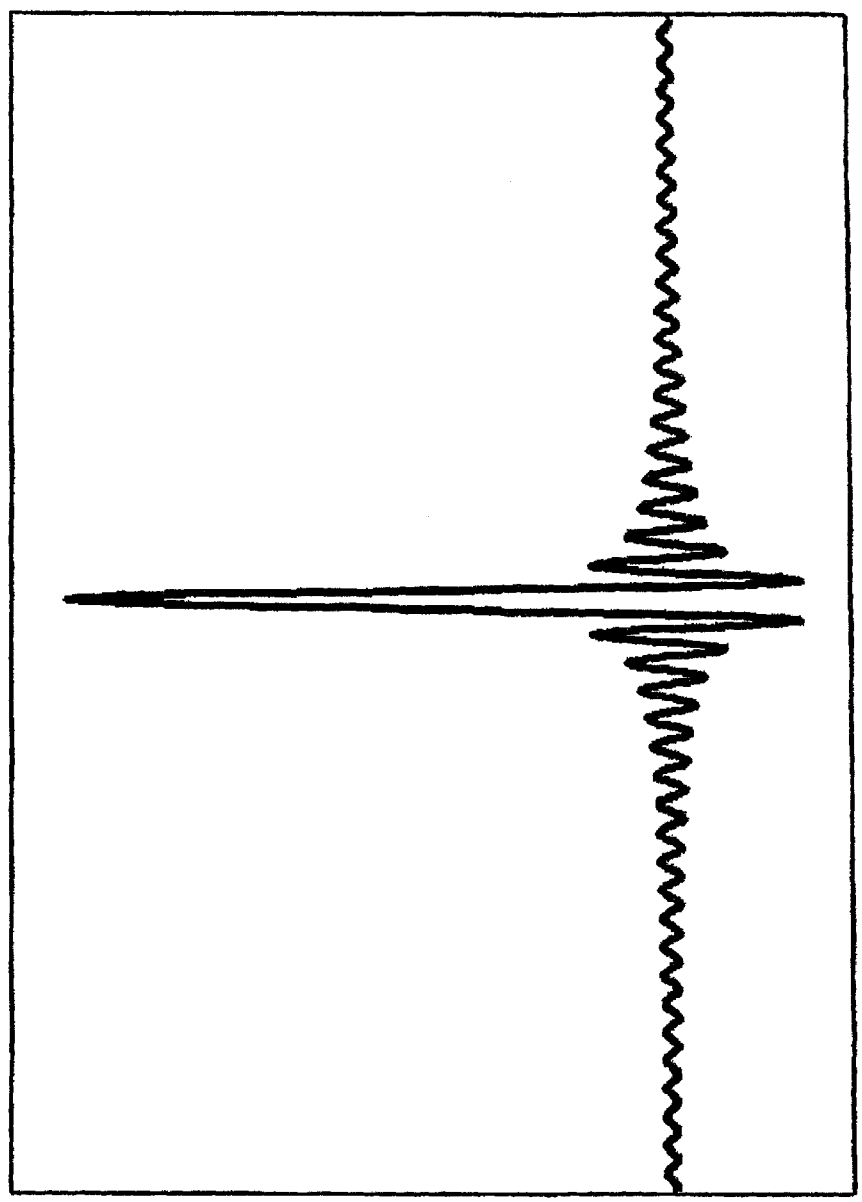

FIG. 2 generic wide band (sin(x)/x) pulse emitted from the function generator 110. The width and frequency content of the pulse is adapted to embrace the resonance frequencies of either the outermost 510 or internal layer 512 of the measurement object 150.

Figure 3:
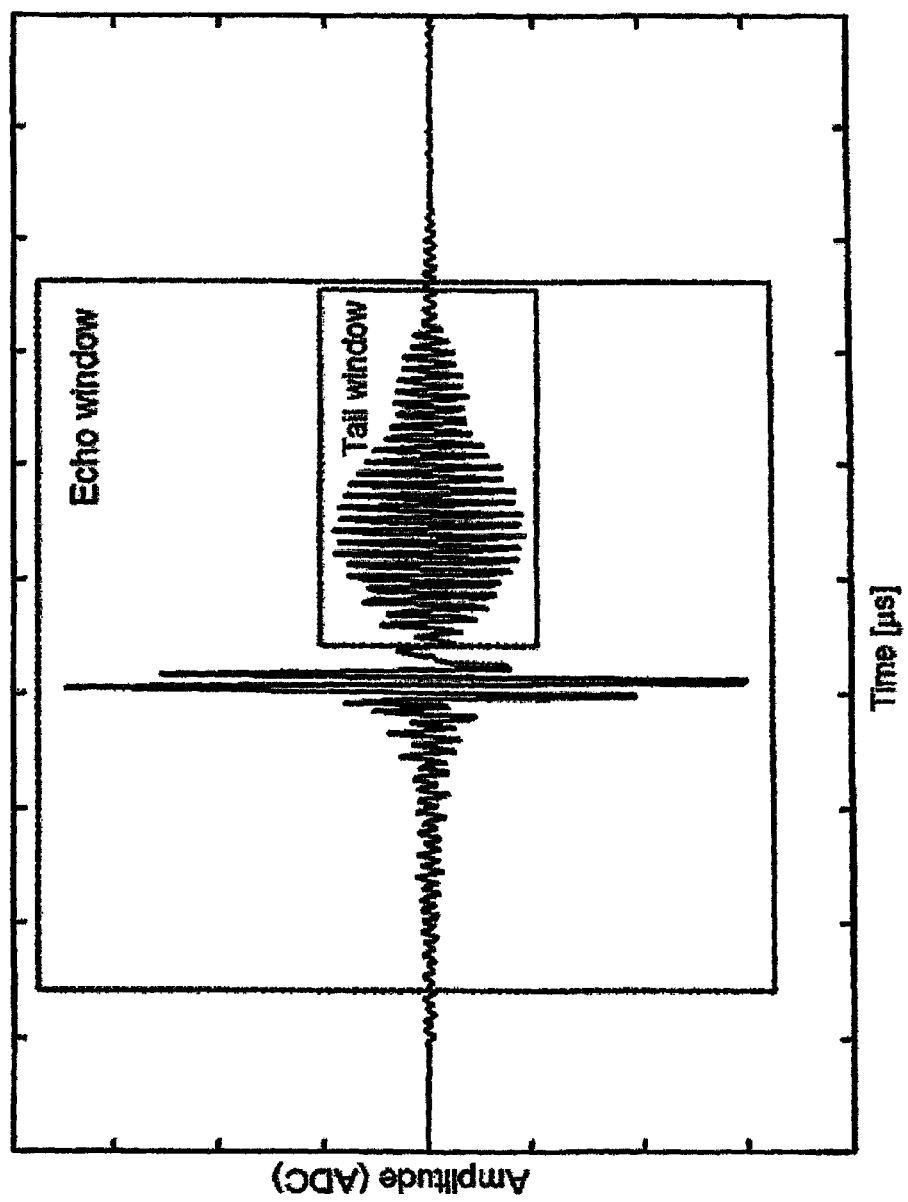

FIG. 3. The primary echo due to the outermost layer of the measurement object 150, associated with a dry intermediate layer 511. The half-wave thickness resonance tail due to the outermost layer 510, from which the outermost layer 510 thickness is determined, is shown in the time window. ADC is an abbreviation for analogue to digital converter.

Figure 4:
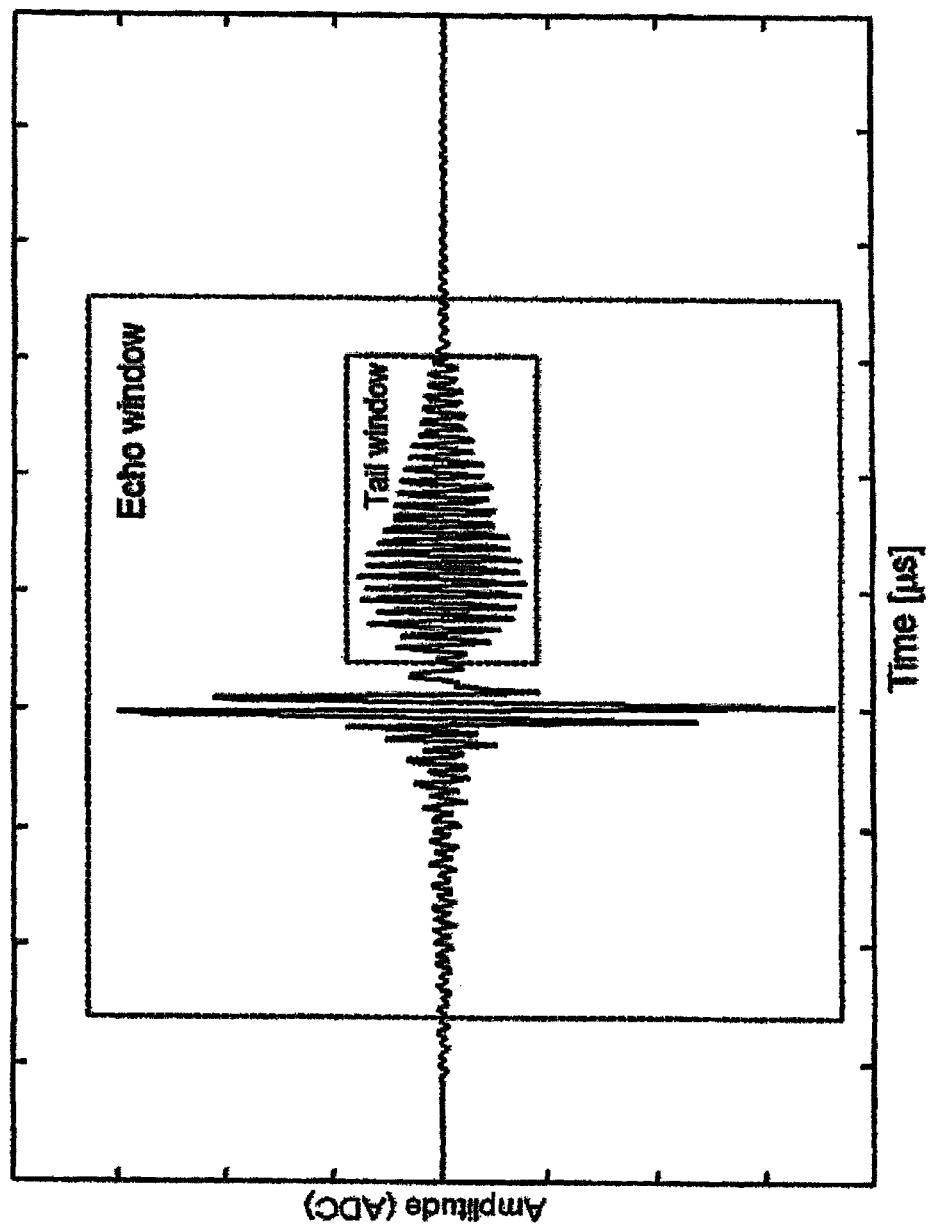

FIG. 4. The primary echo due to the outermost layer of the measurement object 150, for the wet intermediate layer case 511. The half-wave thickness resonance tail due to the outermost layer 510, from which the outermost layer thickness 510 is determined, is shown.

FIG. 5. Piping structure subject to measurement. The labels refer as follows: 510 outermost layer; 511 intermediate layer; 512 internal layer.

Figure 6:
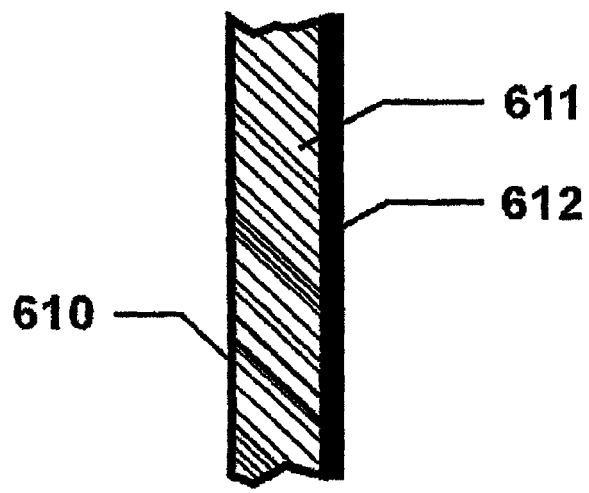

FIG. 6. Sandwich structure subject to measurement. The labels refer as follows: 610 outermost layer; 611 intermediate layer; 612 internal layer.

Figure 7:
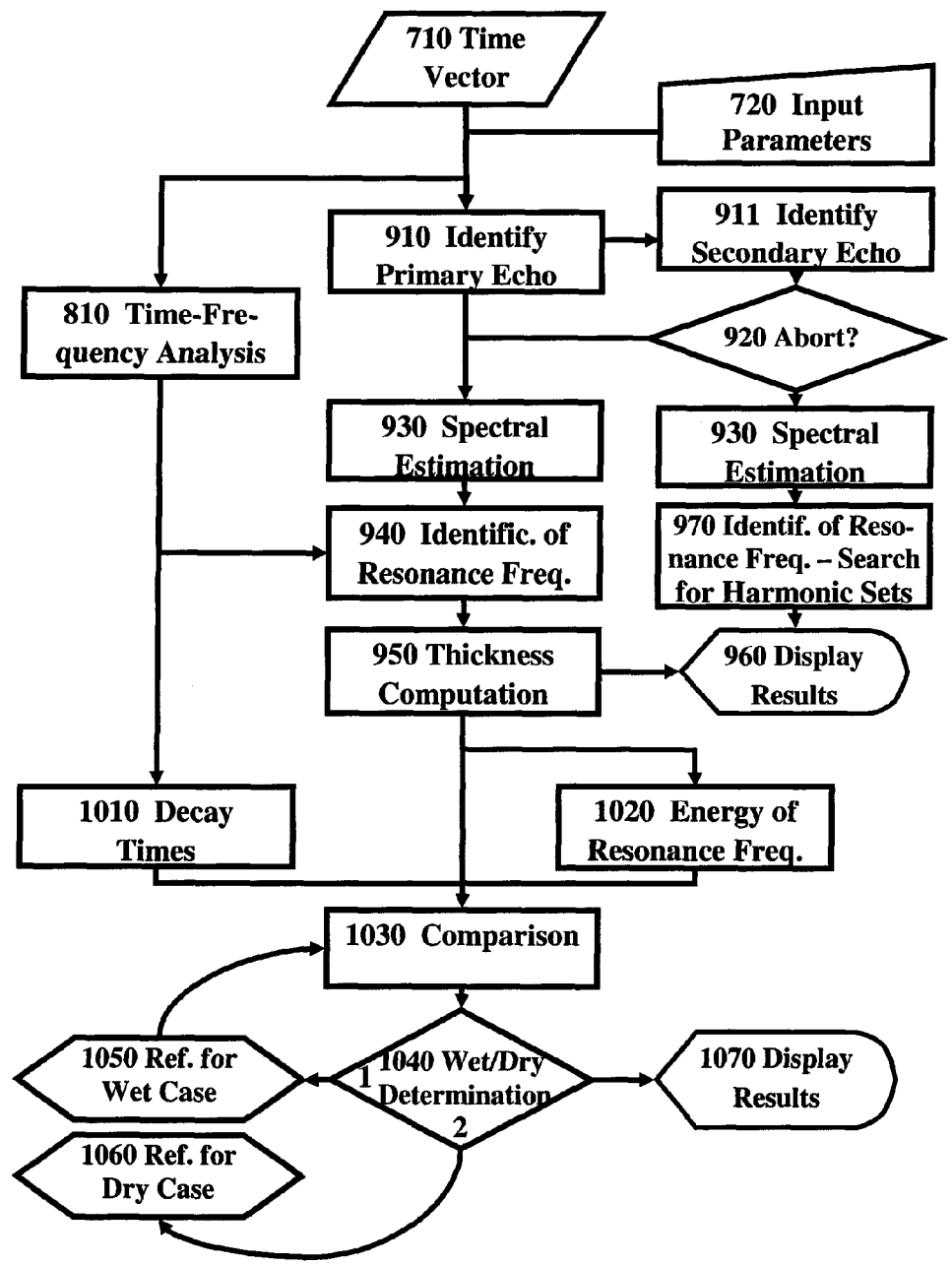

FIG. 7. Flow chart showing the overall structure in the data processing.

Figure 8:
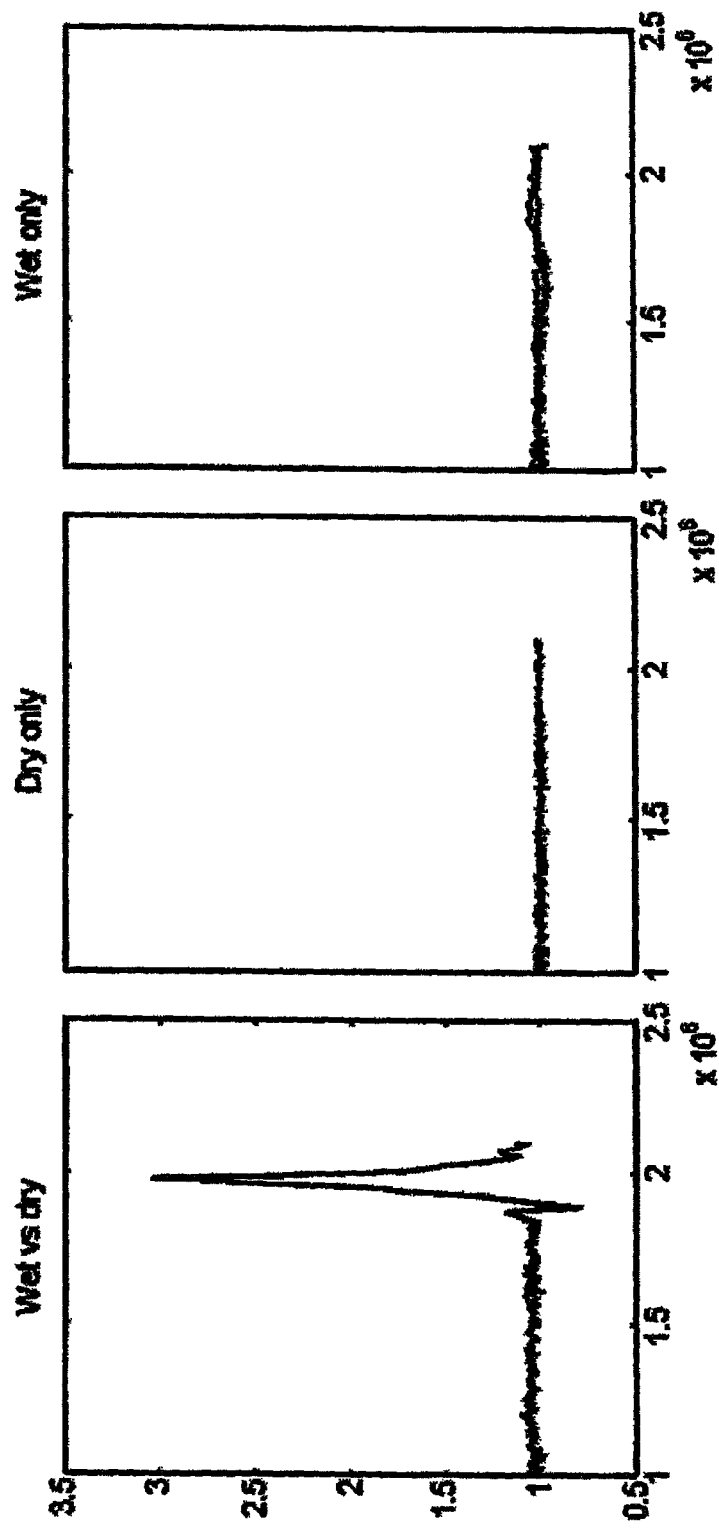

FIG. 8. Division spectra (see text) for wet-dry, dry-dry, and wet-wet combinations of spectra from 6 independent measurements (cf. FIG. 4 and FIG. 5). The resonance frequency for the outermost layer is about 2 MHz in this case. Comparing different measurements recorded for dry (middle plot) and wet (right plot) conditions gives more or less flat spectra, whereas at the resonance frequency there is a significant difference between wet and dry conditions (left plot).

Figure 9:
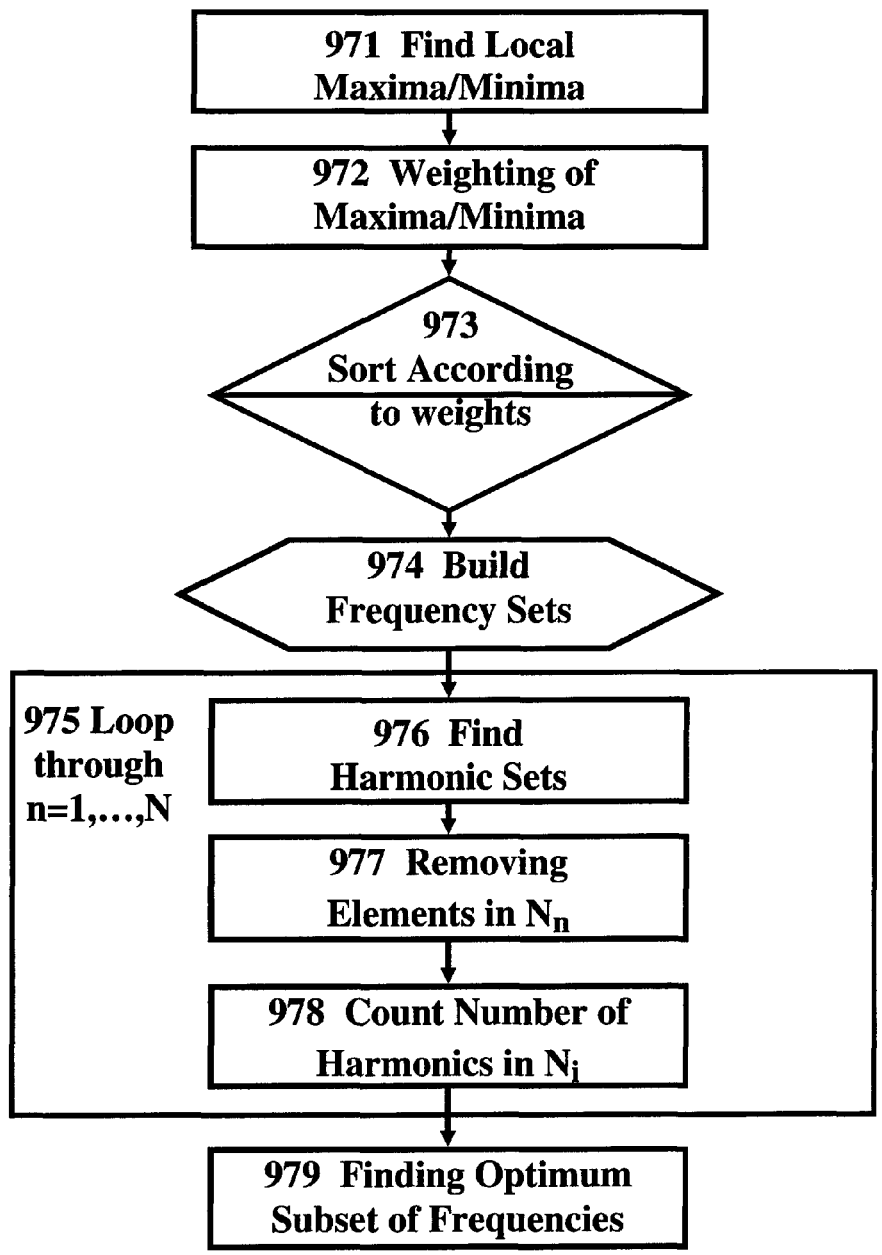

FIG. 9 Flow chart showing the sub-procedure for correctly identifying the harmonic frequencies and assigning the correct order to each.

3 METHODOLOGY

3.1 Reference Measurement at Dry Region

The following description refers mainly to FIG. 1. The control PC 180 comprises suitable software to control the function generator 110 and the data acquisition system (DAQ) 170, by setting relevant parameters. The set 144 of transceivers 140 and 141 is initially clamped at an elevated reference position of the measurement object 150, at which the intermediate layer is presumed not to be wetted by a liquid.

Now the operator enables the function generator 110 (using a button), via the control PC 180, to transmit an electrical wide-band pulse, such as the one in FIG. 2, to the power amplifier 120. The wide-band pulse should at least cover a frequency band, referring to -3 dB, of $$f \in [f_1, f_2], \quad f_i = \frac{c}{2d_i}, \quad i = 1, 2, \tag{1}$$

where c is the sound velocity of the outermost layer 110, and $d_1$ and $d_2$ are respectively the maximum and minimum allowed thicknesses of the outermost layer 510 to be characterized.

Hence, $f_1$ and $f_2$ represent the fundamental half-wave resonances associated with $d_1$ and $d_2$. Preferably, the upper frequency limit should embrace multiple harmonics.

The wide-band pulse is input at the power amplifier (PA) 120, while the DAQ 170 is triggered to start digitizing and storing the electrical signal at its input. The PA 120 preferably amplifies the input wide-band pulse (FIG. 2) linearly to a level slightly less than the maximum input level of the transmitting high-frequency (HF) part of the transceiver 140.

The HF part of the transmitting matching filter 131 minimizes the impedance mismatch between the PA 120 and the transmitting HF part of the transceiver 141, so as to maximize the electrical power input at the transmitting HF part of the transceiver 141.

The HF transmitting part of the transceiver 141 transforms the input electrical pulse to mechanical vibrations. The mechanical vibrations generate a sound wave that propagates through the coupling medium, which may either be a waveguide or a gas, to the measurement object 150. In case of a waveguide, it should preferably have a circular geometry, consist of some solid material, and possess acoustic impedance between that of the active transceiver clement 141 and the outermost layer 510 (FIG. 5).

The sound waves are partially reflected at the outermost layer of the measurement object 150, causing a primary echo. The primary echo travels back through the waveguide, and into the HF receiving part of the transceiver 141. The primary echo is also received at the low-frequency (LF) part of the transceiver 140, but considerably reduced, and considered negligible upon reception.

The HF receiving part of the transceiver 141 is excited by the primary echo to vibrate mechanically, and converts these mechanical vibrations to an electrical HF signal, which is input at the preamplifier 160.

The preamplifier 160 amplifies the input electrical HF signal to a level similar to the input range of the DAQ 170. Possibly, the preamplifier 170 may have embedded a switching circuit that disables the preamplifier output, if—for some reason—the DAQ saturates.

The DAQ 170 digitizes and stores the received HF signal as a reference measurement data result, comprising the primary echo (FIG. 4). The measurement data result will henceforth be referred to as time vector.

3.2 Measurement at Possible Wet Region

Next, the transceiver 140 and 141 is moved to a region of the measurement object 150 that is suspected to contain a wet intermediate layer 511, preferably at a position directly below the presumed dry position. The measurement procedure described in Sec. 3.1 is then repeated, and the received signal is taken to be a measurement data set corresponding to a possible wet region.

An example of a resonance tail due to a wetted intermediate layer 511 is shown in FIG. 4. In this case, a measurement setup such as that described in Sec. 3.1 facilitated the acquired signal. The measurement object 150, immersed in fresh water at room temperature serving as coupling medium, consisted of a 1.5 mm steel plate 610, adjacent to a practically half-infinite layer of water.

3.3 Measurement of Thickness of Internal Layer

To be able to characterize the internal layer, it is required that the water column reaches the internal layer. Moreover, it is required that the thickness of the intermediate layer be greater than $\tau c_w/2$, where $\tau$ and $c_w$ are respectively the time duration of the secondary echo inclusive tail, and sound velocity of the fresh water contained in the intermediate layer.

Upon reception of the above HF signal, the function generator 110 is triggered to transmit another electrical wide-band pulse, similar to the one in FIG. 2, to the power amplifier 120. Now the wide-band pulse should cover at least a frequency band, referring to −3 dB, of $$f \in [f_1, f_2], \quad f_i = \frac{c}{2d_i}, \quad i = 1, 2,$$  (2)

where c is the sound velocity of the internal layer 512, and $d_1$ and $d_2$ are respectively the maximum and minimum allowed thicknesses of the internal layer 512 to be characterized, Hence, $f_1$ and $f_2$ represent the fundamental half-wave resonances associated with $d_1$ and $d_2$ for the internal layer 512. Preferably, the upper frequency limit should embrace multiple harmonics. The present wide-band pulse will be referred to as wide-band LF pulse.

The wide-band LF pulse is input at the PA 120, which preferably amplifies the wide-band LF pulse linearly to a level slightly less than the maximum input level of the transmitting LF part of the transceiver 140.

The LF part of the transmitting matching filter 130 minimizes the impedance mismatch between the PA 120 and the transmitting LF part of the transceiver 140, so as to maximize the electrical power input at the transmitting LF part of the transceiver 140.

The LF transmitting part of the transceiver 140 converts the input electrical pulse to mechanical vibrations. These mechanical vibrations cause sound waves to propagate through the coupling medium to the outermost layer of the measurement object 150.

The sound waves are partially transmitted through the outermost layer of the measurement object 150, proceeding though the intermediate layer (FIG. 5), to be reflected at the internal layer surface 512 (FIG. 5). This reflection will be referred to as the secondary echo.

The secondary echo propagates back through the intermediate layer 511 (FIG. 5), to be partly transmitted through the outermost layer 510 (FIG. 5).

The secondary echo proceeds through the waveguide, into the LF receiving part of the transceiver 140.

The receiving LF part of the transceiver 140 is excited by the secondary echo to vibrate mechanically, and these mechanical vibrations are converted to an electrical LF signal. The electrical LF signal is then input at the preamplifier 160.

The preamplifier 160 amplifies the input electrical LF signal to a level similar to the input range of the DAQ 170.

The DAQ 170 digitizes and stores the received LF signal, comprising the secondary echo.

3.4 Data Analysis

710 Time Vector

The set of real numbers corresponding to voltages from the DAQ unit 170.

720 Input Parameters

Speed of sound of outer layer, c

Speed of sound of wet intermediate layer 511, $c_w$

Length of time window for spectral estimation, N

Expected width of primary echo without resonance tail, W

Spectral estimation methods

Choice of window functions (e.g. Hanning, Bartley)

Sampling frequency, $F_s$

Frequency interval used in transceiver

Expected outer layer 510 thickness

The thickness of the intermediate layer 511, l

Maximum allowed lag of secondary peak from its theoretical arrival, k

Number of datasets in reference memory, M

810 Time-frequency Analysis

Inputs: time signal, spectral estimation technique, N, $F_s$

The power content in the time-frequency domain is estimated, using any standard technique, such as the sliding Fourier transform, or the Wigner distribution. The time of the maximum energy is identified, from this and N the start time of the tail is found, Time-frequency analysis is processing intensive and can be switched off.

Outputs: matrix of power, vector of times (in units of sampling interval), vector of frequencies (in Hz), start of tail time 910 Identify Primary Echo Inputs: time vector, expected width of primary echo Finds the time corresponding to the largest pulse energy, and uses expected width of primary echo to find the start and stop of the echo Outputs: start and stop times of echo 911 Identify Secondary Echo Inputs: $c_w$, l, k, time vector, start and stop times of primary echo The rough peak location of the secondary echo is found from $$\tau_1 = \tau_0 + \frac{2\ell}{c_w},$$

where $\tau_0$ is the time of arrival of the primary echo (which is found as the midpoint between the start time and end time of the echo), l is the thickness of the intermediate layer 511. The nearest local maximum in the signal energy is deemed to be the time of arrival of the secondary echo. If that local maximum falls outside the range given by k, the start and end of secondary echo are left empty.

Outputs: start and stop times of secondary echo

920 Abort?

Inputs: start and stop times of secondary echo

If the inputs are empty, abort the calculation of internal layer 512 thickness because no echo could be identified.

Outputs: whether secondary echo was found

930 Spectral Estimation

Inputs: time vector, spectral estimation method, start and stop times for analysis, window functions, N, $F_s$ The frequency power content of the time signal is estimated using any standard technique, from periodogram based methods to parametric methods, for example using the Yule-Walker model. The estimation is performed in two windows, one comprising the tail only (starting at end of echo lasting to end of echo+N), and one comprising the echo and its tail, starting at the time start of echo−N lasting to end of echo+N.

Outputs: power vector tail, vector with frequencies (in Hz) corresponding to the power values, power vector echo, vector with frequencies (in Hz) corresponding to the power values 940 Identification of Resonance Frequencies Inputs: frequency vector from Time-frequency analysis and/or Spectral estimation, power matrix and/or power vector tail, frequency interval used in transceiver, start of tail time in time-frequency vector Either one or both of the following:
1. The resonance frequency is identified as the maximum energy in the power vector inside the frequency interval of the transceiver 141
2. The resonance frequency is identified as the most prominent exponentially decreasing (in time) frequency in the time-frequency matrix, inside the time interval of the tail and inside the frequency interval determined by frequency interval used in transceiver 141.

Outputs: index into time and frequency vectors corresponding to the resonance frequency 970 Identification of Resonance Frequencies—Search for Harmonic Sets Inputs: frequency vector tail, frequency vector echo, power vector tails power vector echo An elaborate procedure is required to achieve a reliable determination of harmonic orders belonging to frequencies. The procedure is detailed in 971-979 below.

Outputs: harmonic orders, resonance frequencies

950 Thickness Computation

Inputs: c, resonance frequencies, harmonic orders

The layer thickness is computed from $$d = \frac{c}{2 f_{res}}, \quad (2)$$

where $f_{res}$ is the resonance frequency. If the wide band pulse produced by the transceiver 140 and 141 covers several harmonic orders of the resonance frequency, a more reliable method for thickness computation calculates $$d = \left\langle \frac{cn}{2 f_{res}} \right\rangle, \quad (3)$$

where now n is the integer indicating the harmonic order <·> indicates averaging.

Display results.

Outputs: thickness estimates

960 Display Results

1010 Decay Times

Inputs: time-frequency power matrix, vector of frequencies, start of tail time

The characteristic decay time of the resonance in the tail is found.

Outputs: the decay time of the resonance frequency

1020 Energy of Resonance Frequencies

Inputs: power vector tail, power vector echo, index of resonance frequency

Reads the values in the power vectors

Outputs, power at resonance frequency in tail, power at resonance frequency in echo 1030 Comparison Inputs: power of resonance frequency in tail, power vector echo, decay time, reference power of resonance frequency in tail, reference power vector echo, reference decay time Reference variables are vectors comprising several previous realisations, the exact to number determined by the input variable M (see above under Input parameters)

Initalisation of comparison: one or more data sets are recorded at location(s) known to be dry. The readings are analysed using the above steps, and the power spectrum in echo, decay time of resonance frequency in the tails, and lastly the maximum power of the resonance frequency in the tail, are stored. All the features are classified as "dry".

The new data comprising the power of resonance frequencies in tail, power vector echo, and the decay time, are compared with their respective reference values in the following manner:
1. the decay time is subtracted from the reference values, henceforth referred to as difference decay times
2. the power of resonance frequency in the tail is subtracted from the reference values, henceforth referred to as difference powers
3. the power vector echo is divided by the references, from this point referred to as division spectra An example of the output resulting from 3) is illustrated in FIG. 8. Spectra have been calculated for 6 different time sequences, $P_i(f)$, i=1, . . . ,6, with water present in the intermediate layer for i=1,2,3. The plots were produced by dividing pairs of spectra, $P_i(f)/P_j(f)$. To the left is shown results when both spectra correspond to wet conditions (i,j=1,2,3), the middle plot shows dry conditions (i,j=4,5,6), whereas the leftmost plot shows one each (i=1,2,3 and j=4,5,6). When both spectra correspond to identical conditions, the ratio is flat for all frequencies, whereas for different conditions the resonance frequency of the outermost layer is distinctly different and shows up as a clear feature (a peak in this case) in the division spectrum.

Outputs: division spectra, difference powers, difference decay times

1040 Wet/dry Determination

Inputs: division spectra, difference powers, difference decay times, power vector tail, resonance frequency, previous result (wet/dry), M For each of the comparisons one must determine whether they are consistent with wet or dry conditions This is done in the following manner:
1. decay time: if M wet references and M dry references are available, compute the mean decay time in each case. Classify as "dry" if the decay time is closer to the "dry" mean, and correspondingly for "wet". If not all references are available, do not contribute to the decision, but keep the number for reference.
2. resonance power tail: if M wet references and M dry references are available, compute the mean resonance power tail in each case. Classify as "dry" if the resonance power tail is closer to the "dry" mean, and correspondingly for "wet". If not all references are available, do not contribute to the decision, but keep the number for reference.

3. the division spectra are each analysed for a distinct feature at the resonance frequency. Such a feature indicates change (from wet to dry or from dry to wet). The change/no change results are stored in a vector.

A simple majority voting is then used to classify the measurement as indicating either "dry" or "wet" conditions According to the decision, the power vector tail, the power vector echo, and decay time are stored as a reference in either the "wet" or "dry" class, If the number of stored references is equal to M, the currently obtained results replace the oldest reference.

Output: display result, new reference values,
1050 Reference for the Wet Case
1060 Reference for the Dry Case
1070 Display Results
Undescribed Actions The original time vector is stored.
All display functions in the flow chart imply storage.
971 Find Local Maxima/minima
Inputs: power vector echo, power vector tail, bispectrum vector Finds local maxima in the bispectrum vector and the power vector tail. Finds local minima in the power vector echo.

The union of the three sets is the list of potential harmonic frequency candidates.

Outputs: harmonic frequency candidates
972 Weighting of Maxima/minima
Inputs: harmonic frequency candidates, power vector echo, power vector tail, bispectrum vector, filter size 1. Initialise weights vectors with values zero except at harmonic frequency candidates, where the value from the power vectors is used for bispectrum and tail. The weight vectors are normalised to the largest value in each case, e.g. all weights from the bispectrum candidate frequencies are normalised to the maximum value in the bispectrum vector.
2. subtract the power vector echo with its filtered version. The difference at the local minima defines the weight in this case. Normalise.
3. One now has available three sets of weights, $W_{bisp}$, $W_{tail}$, $W_{echo}$, each normalised so the largest weight is 1.
4. For each set, scale the weights by $$W_j(i) = W_j(i) \prod_{k \neq j} \exp(-d_k)$$

where $d_k$ is the shortest distance to a non-zero weight in set k, $W_j(I)$ is the ith element of the jth set.
5. sum the weights from each set to obtain a single weight vector The ensuing weight vector gives weight to large peaks/deep minima in the respective power vectors, but penalises each weight if it is far from frequencies in the other sets. Weights are real numbers between 0 and 1.

Outputs: weights assigned to each harmonic frequency candidate
973 Sort According to Weights
Inputs: weights, harmonic frequency candidates
Sorts the weights vector, and uses the sort indices to rearrange the harmonic frequency candidates so that they are listed in decreasing weighted order.
Outputs: sorted harmonic frequency candidates 974 Build Frequency Sets
Inputs: sorted harmonic frequency candidates, weights, frequency weights threshold
1. Reject all candidate frequencies below the threshold
2. Rearrange frequency candidates into sets. If there are N candidates, then build N lists $\{f_1, \ldots, f_N\}$, $\{f_1, \ldots, f_{N-1}\}$, and so on, where the smallest weighted frequency in the previous list is progressively removed. Bach list is henceforth known as a frequency set.

Each frequency set is denoted $F_n$.
Outputs: frequency sets $\{F_1, F_2, \ldots, F_N\}$
975 Loop Through n=1, . . . ,N
976 Find Harmonic Sets
Input: Frequency sets $\{F_1, F_2, \ldots, F_N\}$, integer tolerance, expected maximum thickness, frequency interval used in transceiver The harmonic sets for one frequency list $F_i$ is computed as follows: initially a n×n matrix with filled with all possible ratios of frequencies is found, $$M'_{ij} = \frac{f_i}{f_j}$$

The matrix M' is used to build a larger matrix M by concatenating kM', k=1,2, . . . ,$k_{max}$ as follows:

$$M = \begin{bmatrix} 1 \cdot M' \\ \vdots \\ k_{max} \cdot M' \end{bmatrix}$$

The integer $k_{max}$ is computed from the maximum allowed thickness, a user input.

The next step is to round all elements in M to their nearest integer, and compare the difference between the integer values and the frequency ratios in M. An element is deemed an integer if this difference is less than a user specified threshold, typically 0.1, and a matrix N where all non-integer elements in M equal zero if found. The rows in N identify the harmonic sets: for a given $N_{ij}$ element the value corresponds to the harmonic order of frequency $f_j$ in the frequency list.

Output: Set of integer matrices $\{N_1, N_2, \ldots, N_N\}$.
977 Removing Elements in $N_n$:
Input: Set of integer matrices $\{N_1, N_2, \ldots, N_n\}$, expected maximum thickness) frequency interval used in transceiver The harmonic order matrices $N_n$ are significantly reduced by removing rows containing a value above the max order $k_{max}$. All duplicate rows are removed, and rows giving a thickness above the user input maximum value are removed, Outputs: Set of reduced integer matrices $\{N_1, N_2, \ldots, N_n\}$
978 Count Number of Harmonics in $N_i$:
Input: Set of reduced integer matrices $\{N_1, N_2, \ldots, N_n\}$.
For each $N_n$, the harmonic set with the largest number of unique frequencies are recorded. The numbers are stored in a vector $\Phi$.

Output: Vector $\Phi$ of maximum number of unique sets.
979 Finding Optimum Subset of Frequencies:
Input: Vector $\Phi$ of maximum number of unique sets, number of frequencies in each frequency set, set of reduced integer matrices $\{N_1, N_2, \ldots, N_n\}$.

The aim is to find the optimum subset of the original frequency list. Each subset is associated with a number of unique harmonics stored in $\Phi$. In addition, each subset has a number of frequencies.

The optimal subset is found by finding the highest ratio of $\Phi$ divided by the number of frequencies in the list, neglecting the trivial case for only a single frequency. In this process we have accomplished both a rejection of frequencies, and obtained harmonic sets.

Output: Indices to optimal subset of frequencies, set of harmonics.

3.5 Liquid Level Determination

Upon positive detection of liquid in the intermediate layer 511, the transceiver 140 and 141 is moved upwards in steps of, say 10 mm, towards elevated regions of the measurement object 150. Meanwhile, the procedures described in Secs. 3.1 to 3.4 are repeatedly performed, to determine at which level the liquid surface occurs.

The invention claimed is:

1. Apparatus for determining moisture ingress in an insulating layer surrounding a pipe, said insulating layer being surrounded by a tubular jacket, said apparatus comprising an acoustic transducer in communication with an exciter adapted to provide a brief and broad banded acoustic signal which by propagation in the material of the jacket has a wavelength corresponding to twice the thickness of the jacket or an odd multiple part of twice the thickness of the jacket, a signalling processing receiver in communication with the transducer and adapted to receive and process a reverberation signal emitted by the jacket in response to transmitting into the jacket the brief and broad banded output signal from the transducer, wherein the signal processor is adapted to carry out a frequency analysis of the received reverberation signal for producing a frequency response curve, to establish features of the frequency response curve being characteristic of insulation material containing moisture on the inside of the jacket, and to provide an indication being specific to the moisture ingress.

2. The apparatus of claim 1, wherein the broad banded transducer is adapted for operating at a band centre frequency of about 4.3 MHz.

3. The apparatus of claim 2, wherein the signal processing device is operable to normalize the frequency response curve and on basis of the normalized frequency response curve to compute an actual moisture content value.

4. The apparatus of claim 1, wherein the signal processing device is operable to normalize the frequency response curve and on the basis of the normalized frequency response curve to compute an actual moisture content value.

5. A method of using the apparatus of claim 1 to determine moisture ingress in an insulating layer surrounding a pipe, said insulation layer being surrounded by a tubular jacket, said method comprising
providing a brief and broad banded acoustic signal which by propagation in the jacket has a wavelength corresponding to twice the thickness of the jacket or an odd multiple of twice the thickness of the jacket,
receiving and processing a reverberation signal emitted from the jacket in response to sending into the jacket the brief and broad banded output signal from the transducer,
producing a frequency response curve from the received reverberation signal,
analyzing features of the response curve to determine moisture characteristics of the insulation material, and
outputting an indication being specific to the moisture ingress.

6. The method of claim 5, further comprising adapting the broad banded transducer to operate with a band centered frequency of about 4.3 MHz.

7. The method of claim 6, further comprising adapting the signal processing device to normalize the frequency response curve, and to calculate an actual moisture content value based on the normalized frequency response curve.

8. The method of claim 5, further comprising adapting the signal processing device to normalize the frequency response curve, and to calculate an actual moisture content value based on the normalized frequency response curve.

* * * * *